(12) United States Patent
McDonald et al.

(10) Patent No.: US 6,962,090 B2
(45) Date of Patent: Nov. 8, 2005

(54) HEATED STAINLESS STEEL EMISSIONS CANISTER

(75) Inventors: Joseph Fitzgerald McDonald, Ann Arbor, MI (US); William Martin Silvis, Ann Arbor, MI (US); Norbert Kreft, Ann Arbor, MI (US); Gerald Marek, Ann Arbor, MI (US)

(73) Assignee: AVL North America Inc., Plymouth, MI (US)

( * ) Notice: Subject to any disclaimer, the term of this patent is extended or adjusted under 35 U.S.C. 154(b) by 416 days.

(21) Appl. No.: 10/085,421

(22) Filed: Feb. 28, 2002

(65) Prior Publication Data

US 2003/0159496 A1 Aug. 28, 2003

(51) Int. Cl.$^7$ .............................. G01F 15/02; G01N 1/22
(52) U.S. Cl. ................................ 73/863.03; 73/864.73; 73/23.31
(58) Field of Search ........................ 73/863.03, 863.11, 73/864.73, 23.31, 23.32

(56) References Cited

U.S. PATENT DOCUMENTS

| | | | | | |
|---|---|---|---|---|---|
| 4,823,591 | A | * | 4/1989 | Lewis ......................... | 73/1.26 |
| 5,445,035 | A | * | 8/1995 | Delajoud ................... | 73/861.52 |
| 5,756,360 | A | * | 5/1998 | Harvey et al. ............ | 73/863.03 |
| 5,868,159 | A | * | 2/1999 | Loan et al. ................ | 137/334 |
| 6,282,944 | B1 | * | 9/2001 | Bornemann ............... | 73/23.31 |
| 6,293,161 | B1 | | 9/2001 | Hanashiro et al. ........ | 73/863.11 |
| 2002/0082783 | A1 | * | 6/2002 | Grosshart .................. | 702/50 |

FOREIGN PATENT DOCUMENTS

| | | | | |
|---|---|---|---|---|
| JP | 63083629 | A | * 4/1988 | ................ 73/23.31 |
| JP | 11344425 | A | * 12/1999 | |

OTHER PUBLICATIONS

Fitch et al., "Pressure–Based Mass–Flow Control Using Thermopneumatically–Actuated Microvalves", Proceedings, Sensors and Actuators Workshop, 1998 no month, pp. 162–165.*

(Continued)

*Primary Examiner*—Michael Cygan
(74) *Attorney, Agent, or Firm*—Carlson, Gaskey & Olds

(57) ABSTRACT

An exhaust gas measurement system is provided that includes a probe to find a sample exhaust gas passageway for collecting exhaust gas. A stainless steel canister is fluidly connected to the probe for storing the exhaust gas. A pump fluidly interconnects the probe and the canister for transferring the exhaust gas from the probe to the canister. A pressure mass flow controller fluidly interconnects the probe and the canister and produces an exhaust gas flow measurement corresponding to the flow of the exhaust gas from the probe to the canister. A temperature sensor senses a temperature of the exhaust gas proximate to the pressure mass flow controller. The temperature sensor corrects the exhaust gas flow measurement based upon the temperature sensed. A pressure sensor senses a pressure of the exhaust gas proximate to the pressure mass flow controller. The temperature sensor corrects the exhaust gas flow measurement based upon the pressure sensed. The mass flow controller can be controlled by an external source to account for flow changes in the CVS system. A heating device heats the stainless steel canister and other components of the exhaust gas measurement system such as the pressure mass flow controller to a temperature of preferably approximately 191° C. Another heated pressure mass flow controller may also be used to determine the amount of exhaust gas that is transferred from the canister to an analyzer for the actual determination of the hydrocarbons.

7 Claims, 1 Drawing Sheet

OTHER PUBLICATIONS

MKS Instruments Brochure, "Pressure–Based Mass–Flo® Controller for Ion Implant Applications", Jun. 2001.*

Code of Federal Regulations Title 40 Protection of Environment, Chapter I Environment Protection Agency, Subchapter C Air Programs, Part 86 Control of Emissions From New and In–Use Highway Vehicles, Engines Subpart N Emission Regulations For New Otto–Cycle And Diesel Heavyduty and Engines Gaseous And Particulate Exhaust Test Procedures, pp 2–10, Current through Jan. 18, 2002.

Ken–ichi Akiyama, Collection of Exhaust Hydrocarbons by a Heated Stanless Steel Canister and a Heated Stainless Steel Syring, pp. 114–123, Feb. 28–Mar. 3, 1994.

* cited by examiner

HEATED STAINLESS STEEL EMISSIONS CANISTER

BACKGROUND OF THE INVENTION

This invention relates to an exhaust gas measurement system, and more particularly, the invention relates to a system for more accurately measuring hydrocarbon emissions in vehicle exhaust.

Modern vehicles must meet stringent government guidelines that set forth the allowable amount of products of combustion in the vehicle's exhaust, such as CO, $NO_x$, and hydrocarbons. Not only does the government set the permissible amount of each product of combustion, but the government also mandates some of the testing equipment and procedures that must be employed when measuring vehicle exhaust to ensure that the vehicle complies with the government rules. For example, the EPA has promulgated rules governing emissions from heavy-duty diesel-fueled engines as set forth at 40 CFR §§86.1310-2007. While the Rules permit measurement systems of various configurations, the Rules also mandate that particular procedures must be used.

The challenge in ensuring compliance with emissions guidelines is accurately measuring the products of combustion during transient vehicle operating conditions. That is, the products of combustion change as the vehicle is run through a federally mandated test procedure. This challenge is further complicated by the EPA's desire to lower the permissible amount of products of combustion and the limitations of current testing equipment. Many in the automobile industry object to the new Rules as being very difficult to comply with and fear that inaccuracies would result causing complying vehicles to fail. Current configurations of emissions testing equipment cannot meet the EPA's proposed requirements regarding hydrocarbon measurement, and new systems must be developed.

A typical constant volume emissions sampler is shown in Figure N07-1 in the Rules referred to above. The sampler includes a probe that collects exhaust gases from a vehicle exhaust pipe. The Rules describe one system for continuous hydrocarbon measurement used to measure the entire vehicle exhaust volume in which the exhaust gases flow through conduits to an inline heated flame ionization detector (HFID) to measure the hydrocarbons. The conduits and other system component leading up to and including the HFID typically must be heated to 191° C. to prevent the larger chain hydrocarbons from condensing within the system prior to measurement. The analyzer signal is integrated over the duration of the test to determine the quantity of hydrocarbons. Venturis are typically used to control the flow rate of the gases through the measuring system, which assumes a constant flow rate, although transients during the test prevent a constant flow rate from being maintained. As a result, inaccuracies in continuously measuring the products of combustion in line with the HFID occur, which may cause some vehicles to fail the test when they should have passed and vice versa because of the dynamic nature of the emissions the HC analyzer has to be operated in a relatively high range.

The Rules describe another system for measuring hydrocarbons that employ plastic bags that store only a portion of the vehicle's exhaust. The exhaust gases are collected in the bags and then after the completion of the test the bags are transferred through conduits to an analyzer where all of the hydrocarbons may be measured. Collection of the gases within the bags is a "pneumatic integration" of the diluted engine exhaust; the concentration in the bags is constant, which makes the use of a low analyzer range possible thereby increasing the accuracy. Again, much of the exhaust measurement system is heated to 191° C. to prevent the gasses from condensing. The Rules require that the bags also must be heated to 191° C. However, bags currently available may only be heated to about 40° C., which would only permit the smaller chain hydrocarbons to be measured. Hydrocarbons will be absorbed in the bag material, which reduces accuracy.

Using stainless steel canisters for storage of hydrocarbons at up to 160° for subsequent measurement has been proposed in the prior art. The canister is vacated and filled at a constant flow rate. When the canister is above atmospheric pressure, the exhaust gas is vented from the canister to an analyzer to measure the. Since the canister is a rigid container, it is not operated at constant atmospheric pressure as is a typical plastic bag, which makes it difficult to accurately control the flow rate and measure the sample. The disclosed system does not meet the requirements of the Rules, nor does the system disclose how the system accurately controls the flow rate of the exhaust gases into and out of the canister. Therefore, what is needed is an exhaust gas measurement system that meets the requirements of the Rules while providing accurate results to the automobile industry.

SUMMARY OF THE INVENTION AND ADVANTAGES

The present invention provides an exhaust gas measurement system including a probe to find a sample exhaust gas passageway for collecting exhaust gas. A stainless steel canister is fluidly connected to the probe for storing the exhaust gas. A pump fluidly interconnects the probe and the canister for transferring the exhaust gas from the probe to the canister. A mass flow controller fluidly interconnects the probe and the canister and produces an exhaust gas flow measurement corresponding to the flow of the exhaust gas from the probe to the canister. The mass flow controller is based on the differential pressure drop across a laminar flow element (LFE) or a similar device and is pressure and temperature compensated; the controller also incorporates a control valve. A temperature sensor measures the temperature of the exhaust gas proximate to the mass flow controller. The temperature sensor corrects the exhaust gas flow measurement based upon the temperature sensed. A pressure sensor senses the absolute pressure of the exhaust gas proximate to the pressure mass flow controller. The pressure sensor corrects the exhaust gas flow measurement based upon the pressure sensed. The mass flow controller is set to a constant flow rate but can alternatively be controlled by an external source to account for flow changes in the CVS system. A heating device heats the stainless steel canister and other components of the exhaust gas measurement system such as the pressure mass flow controller to a temperature of preferably 191° C. At this temperature hydrocarbons may be measured. Another heated mass flow controller may also be used to determine the amount of exhaust gas that is transferred from the canister to an analyzer for the actual determination of the hydrocarbons.

Accordingly, the above invention provides an exhaust gas measurement system that meets the requirements of the Rules while providing accurate results to the automobile industry.

BRIEF DESCRIPTION OF THE DRAWING

Other advantages of the present invention can be understood by reference to the following detailed description when considered in connection with the accompanying drawing wherein the FIGURE is a schematic of the present invention exhaust gas measurement system.

DETAILED DESCRIPTION OF THE PREFERRED EMBODIMENT

Figure 1:
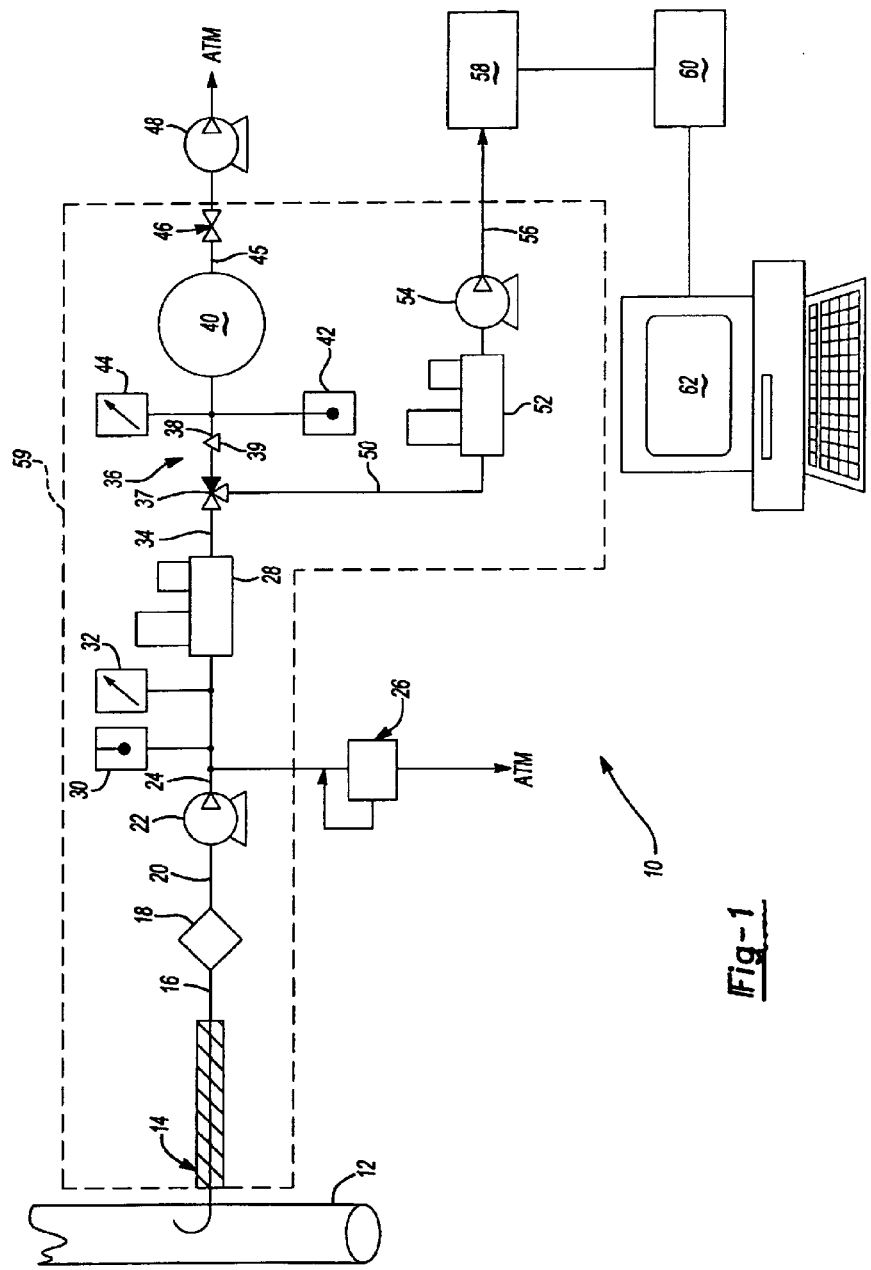

An exhaust gas measurement system 10 is shown in the FIGURE. A constant volume sampler 12 is connected via exhaust pipe to a vehicle engine. The permissible amount of products of combustion that a particular vehicle engine may produce is regulated by the EPA. For example, the EPA has determined that it is desirable to limit the amount of the total hydrocarbon emissions from a vehicle. The EPA has promulgated a Rule mandating that the hydrocarbons must be measured at 191° C. However, it is contemplated that other temperatures may be acceptable in the future.

The system 10 of the present invention includes a heated probe 14 that defines a sample exhaust gas passageway for collecting the exhaust gases from the sampler 12. A conduit 16 transfers the exhaust gases from the probe 14 to a filter 18 where the particulate matter from the exhaust gases is removed. For a test procedure in which hydrocarbons are measured, the filter will typically discarded if significant hydrocarbon hang-ups occur or the pressure drop across the filter becomes too high. A conduit 20 transfers the exhaust gases from the filter 18 to a pump 22, which moves the exhaust gases through the system 10. The pump 22 transfers the exhaust gases through conduits 24, 34, and 38 to a stainless steel canister 40, which is preferably electro polished or glass lined, where the exhaust gases are stored for subsequent analysis. A back pressure regulator 26 may be connected to the conduit 24 to control the pressure of the exhaust gases within the system 10. Exhaust gas pressure exceeding a desired pressure is vented to the atmosphere by the regulator 26.

A mass flow controller 28 may be utilized between the probe 14 and the canister 40 to measure and control the amount of exhaust gases flowing into the canister 40. A very accurate measurement is required to ensure a precise analysis of the products of combustion. Thermal mass flow controllers have been used in the prior art and their accuracy is adversely affected by high temperatures. However, for hydrocarbon emissions analysis the exhaust gases must be heated, for example, up to 191° C. Thermal mass flow controllers are only available for lower temperatures. As a result, thermal mass flow controllers cannot produce accurate enough measurements for the exhaust gas to ensure that reliable analysis of the products of combustion is obtained. Accordingly, the present invention utilizes a pressure mass flow controller based upon the pressure drop across a LFE.

The reading of the pressure mass flow controller 28 is corrected by a temperature sensor 30 and a pressure sensor 32 that respectively read the temperature and pressure proximate to the pressure mass flow controller 28. Utilizing a pressure mass flow controller is particularly helpful when used in conjunction with the canister 40. The plastic sample bags typically used in the prior art have very flexible walls upon which the atmosphere exerts pressure. The effects of the atmosphere on the plastic bags and the other components of the system 10 simplifies the measurement of the exhaust gases flowing through the system. However, the canister 40 of the present invention has rigid walls making the effects of the atmospheric pressure negligible. As a result, precise control and measurement of the exhaust gases flowing into the canister 40 is more difficult to achieve.

A valve assembly 36 includes a valve 37 placed between the conduits 34, 38 and another conduit 50 leading to the analysis equipment. The valve 37 may either close the conduit 34 from the conduits 38 and 50 or close the conduit 50 from the conduits 34 and 38. The valve assembly 36 also includes a valve 39 placed between the conduit 38 and the canister 40 to prevent it from filling when it is in an evacuated state or from evacuating when it is above atmospheric pressure. A conduit 45 connects the canister 40 to a pump 48. A valve 46 is connected between the canister 40 and pump 48. The pump 48 is used to evacuate the contents of the canister 40 prior to collecting the exhaust gas for analysis so that the contents of the canister do not effect the results. In operation, the valve 46 is opened and the pump 48 evacuates the contents of the canister 40. The valve 46 is then closed to maintain a vacuum within the canister 40. The valve 37 is actuated to close the conduit 50 such that the conduits 34 and 38 are fluidly connected. Of course, it is to be understood that any number of suitable value arrangements may be used.

Once the exhaust gases have been transferred by pump 22 from the probe 14 to the canister 40 and measured by the pressure mass flow controller 28, the contents of the canister 40 may be analyzed to determine the quantity of the products of combustion. The valve 37 is actuated to close the conduit 34 and connect the conduits 38 and 50. The flow of exhaust gases from the canister 40 are measured by a second mass flow controller 52 that is corrected by a temperature 42 and a pressure sensor 44, similar in manner to that of mass flow controller 28. A pump 54 is used to evacuate the contents of canister 40 and transfers the exhaust gases through conduits 50 and 56 to an analyzer 58, such as a flame ionization detector a gas chromatograph. Evacuating the contents of the canister under its own pressure would not transfer all of the products of combustion to the analyzer.

A heating device such as an oven 59 is typically used to heat the pumps 22, 48, 54, the pressure mass flow controllers 28, 52, the sensors 30, 32, 42, 44, and the valves 37, 39 and 46. Preferably, the gases are transferred to the analyzer, which is typically heated separately, by a heated line. The heating device 59 maintains the temperature of these components at 191° C. to prevent condensation of hydrocarbons and permit all the hydrocarbons to be measured by the analyzer 58. Information from the analyzer 58 the pumps, the mass flow controllers, the sensors, and the valves are read and controlled by hardware and software 60. The results from the analyzer and the hardware and software are sent to an output or data recording device 62, which indicates whether the vehicle passed or failed based upon the EPA standards.

The system 10 described above may be used for different system configurations and for testing products of combustion other than hydrocarbons. For example, the $CO_2$ within the canister may be measured to calculate engine fuel efficiency. Heating bags increases outgassing of the exhaust sample collected with the bags and overstates the fuel efficiency of the engine. The stainless steel canister of the present invention may be heated without increasing outgassing thereby providing a more accurate fuel efficiency.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

What is claimed is:

1. An exhaust gas measurement system comprising:

a probe defining a sample exhaust gas passageway for collecting exhaust gas;

a stainless steel canister fluidly connected to said probe for storing the exhaust gas;

a pump fluidly interconnected between said probe and said canister for transferring the exhaust gas from said probe to said canister;

a pressure mass flow controller fluidly interconnected between said probe and said canister producing a exhaust gas flow measurement corresponding to the flow of the exhaust gas from said probe to said canister;

a temperature sensor for sensing a temperature of the exhaust gas proximate to said pressure mass flow controller, said temperature sensor correcting said exhaust gas flow measurement based upon said temperature;

a pressure sensor for sensing a pressure of the exhaust gas proximate to said pressure mass flow controller said pressure sensor correcting said exhaust gas flow measurement based upon said pressure;

heating device heating said stainless steel canister and said pressure mass flow controller;

wherein an exhaust gas analyzer is fluidly connected to said canister;

wherein a second pump is fluidly interconnected between said canister and said analyzer for transferring the stored exhaust gas from said canister to said analyzer; and wherein a second pressure mass flow controller fluidly is interconnected between said canister and said analyzer producing a second exhaust gas flow measurement corresponding to the flow of exhaust gas from said canister to said analyzer, further including a second temperature sensor for sensing a second temperature of the exhaust gas proximate to said second pressure mass flow controller, said second temperature sensor correcting said second exhaust flow measurement based upon said second temperature, and a second pressure sensor for sensing a second pressure of the exhaust gas proximate to said second pressure mass flow controller, said second temperature sensor correcting said second exhaust flow measurement based upon said second pressure.

2. The system according to claim 1, wherein said heating device heating said second pressure mass flow controller.

3. The system according to claim 2, wherein said heating device heats said second pressure mass flow controller to approximately 191° C.

4. A method of measuring products of combustion in exhaust gases comprising the steps of:

a) sampling exhaust gases from an exhaust source;

b) pumping the exhaust gases to a canister;

c) measuring the amount of exhaust gases entering the canister with a pressure mass flow controller; and d) heating the canister to a desired temperature to prevent condensation of a portion of the products of combustion;

e) pumping the exhaust gases from the canister to an analyzer;

f) determining the portion of the products of combustion with the analyzer; and g) measuring the amount of exhaust gases flowing to the analyzer with a second pressure mass flow controller.

5. The method according to claim 4, wherein step g) includes measuring a second temperature of the exhaust gases proximate to the second pressure mass flow controller and adjusting the second mass flow controller to more accurately measure the amount of exhaust gases in response to the measured second temperature.

6. The method according to claim 4, wherein step g) includes measuring a second pressure of the exhaust gases proximate to the second pressure mass flow controller and adjusting the second mass flow controller to more accurately measure the amount of exhaust gases in response to the measured second pressure.

7. The method according to claim 4, wherein step d) includes heating the second mass flow controller to approximately 191° C.

* * * * *